(12) United States Patent
Xu et al.

(10) Patent No.: US 12,194,469 B2
(45) Date of Patent: Jan. 14, 2025

(54) FLOW CELL AND BIOCHEMICAL SUBSTANCE REACTION DEVICE USING THE FLOW CELL

(71) Applicant: MGI Tech Co., Ltd., Shenzhen (CN)

(72) Inventors: Hong Xu, Shenzhen (CN); Ping Mei, Shenzhen (CN); Yong Gan, Shenzhen (CN); Joon Mo Yang, Sanjose, CA (US); Jody Beecher, San Jose, CA (US); Teresa Woo, San Jose, CA (US)

(73) Assignee: MGI Tech Co., Ltd., Shenzhen (CN)

( * ) Notice: Subject to any disclaimer, the term of this patent is extended or adjusted under 35 U.S.C. 154(b) by 308 days.

(21) Appl. No.: 17/763,270

(22) PCT Filed: Sep. 27, 2019

(86) PCT No.: PCT/CN2019/108642
§ 371 (c)(1),
(2) Date: Mar. 24, 2022

(87) PCT Pub. No.: WO2021/056445
PCT Pub. Date: Apr. 1, 2021

(65) Prior Publication Data
US 2022/0339632 A1 Oct. 27, 2022

(51) Int. Cl.
*B01L 3/00* (2006.01)
*C12Q 1/6874* (2018.01)

(52) U.S. Cl.
CPC ............ *B01L 3/565* (2013.01); *C12Q 1/6874* (2013.01); *B01L 2200/027* (2013.01); *B01L 2200/0684* (2013.01); *B01L 2300/0819* (2013.01); *B01L 2300/0877* (2013.01)

(58) Field of Classification Search
CPC ........ G01N 21/63; G01N 21/13; G01N 21/85; G01N 21/0332; G01N 2021/058; G01N 2021/6482; G01N 33/1893; G01N 21/05; G01N 15/1436; G01N 15/0806; B01L 3/565; B01L 2200/027; B01L 2200/0684; B01L 2300/0819; B01L 2300/0877; C12Q 1/6874
USPC ...... 356/432–440, 246, 73; 422/68.1, 82.05; 436/174, 52
See application file for complete search history.

(56) References Cited

U.S. PATENT DOCUMENTS

| 4,732,479 A * | 3/1988 | Tanaka | G01N 15/1434 356/336 |
| 2013/0281305 A1 | 10/2013 | Peck et al. | |
| 2014/0248617 A1 * | 9/2014 | Shaikh | B01L 3/5027 435/29 |

(Continued)

FOREIGN PATENT DOCUMENTS

CN 104394990 A 3/2015

*Primary Examiner* — Hoa Q Pham
(74) *Attorney, Agent, or Firm* — ScienBiziP, P.C.

(57) ABSTRACT

A flow cell includes a flow cell body. The flow cell body includes a frame and a fluid chamber defined in the flow cell body. The fluid chamber includes a reaction region allowing a fluid flow. A liquid inlet, a liquid outlet, and two exhaust holes connected to the fluid chamber are in the frame. Fluid into the liquid inlet flows through the reaction region in the fluid chamber and flows out through the liquid outlet. The exhaust holes discharge gas generated in the fluid chamber during the fluid flow. A flow cell with integral sealing rings and a biochemical substance reaction device are also disclosed.

13 Claims, 13 Drawing Sheets

(56) References Cited

U.S. PATENT DOCUMENTS

2022/0341848 A1* 10/2022 Jiang .................. G01N 21/85
2023/0158496 A1* 5/2023 Cui ...................... C12M 1/00
                                                            435/287.2

* cited by examiner

FLOW CELL AND BIOCHEMICAL SUBSTANCE REACTION DEVICE USING THE FLOW CELL

FIELD

The subject matter relates to a flow cell carrying a sample for reaction in a field of biochemical reaction and a biochemical substance reaction device using the flow cell.

BACKGROUND

In a field of biochemical analysis, a flow cell, which functions as a sample carrier for carrying a sample of biochemical, and detection and analysis of the sample happen on the flow cell. The flow cell includes a cavity for carrying the sample and fluids. In a case of gene sequencing, the flow cell is a sequencing chip. In other cases, the flow cell can be used as other sample carriers. A current situation of the flow cell is illustrated by taking a sequencing chip as an example.

In a field of gene sequencing, the sequencing chip is usually used as a disposable item of a biochemical substance reaction device. During the sequencing, the sequencing chip carries a sample, and a biochemical reaction with a fluorescence labeling of the sample are performed on the chip. At present, a second-generation sequencing technology mainly includes a fluorescence labeling method based on optical detection, and a chemical sequencing method to identify constituent bases through a change of a concentration of hydrogen ions. Wherein, a detection device of the chemical sequencing method based on the change of the concentration of hydrogen ions to identify constituent bases has the advantages of volume and speed, but also has the disadvantages of homopolymer errors and low throughput. The second-generation sequencing technology based on optical detection and recognition has the highest accuracy of base recognition and the maximum throughput. In the field of sequencing, flow cell is also generally called flow cell, reaction cell, chip, sequencing chip, gene sequencing chip, or cartridge. The common English names are flow cell, flowcell, chip, chip kit, and cartridge.

During the second-generation sequencing technology, the sample of biochemical first undergoes a biochemical reaction to obtain a reaction product, and then a fluorescence display or a signal of electric of the reaction product is analyzed to obtain a DNA sequence. With the high-throughput advantage of the second-generation sequencing, the flow cell, which integrates a substrate made of silicon wafer, glass, or polymer with a MEMS automation or other precision processing technologies, is a high-tech component. Researchers may quickly select a large number of biological analytes for various purposes such as disease diagnosis and bioterrorism detection. The existing sequencing sample loading flow cell is a thin and narrow channel for fluid. Due to a limitation of the limit of optical diffraction, a sample detection of ultra-high sequencing throughput cannot be realized in a single flow cell. For design reasons, the existing chip uses a negative pressure to pump the reagent for purposes of reagent spreading and replacement, which has problems of large reagent substitution ratio and slow reagent substitution speed, which is not conducive to constructing an ultra-high sequencing throughput sequencing system.

In addition to the above problems, there are also the following problems in prior arts:

(1) A chip with single flow direction can not make full use of a circular wafer. A ratio of a length with a width of the chip is too large, requiring a larger size of a scanning platform of a high-precision imager. The pumping speed under the negative pressure is slow.

(2) Due to a limitation of a size and a weight of a sliding platform of an optical mechanical system of an existing sequencing device, one optical mechanical system can only be equipped with not more than two sequencing platforms with flow cells that work at the same time, which is not conducive to a simultaneous sequencing of multiple flow cells in the ultra-high sequencing throughput sequencing system. Moreover, due to a thermal conduction of a carrying platform of the flow cell, it is impossible to completely decouple working states of multiple flow cells. That is, a sequential or combined operation of multiple flow cells cannot be realized in one sequencing device.

(3) An RFID module is separated from an optical identification tag (QR code), which results in a high cost and a mismatch risk of the sequencing chip.

(4) During processes of inputting and outputting reagents of the flow cell, a sealing ring is fixed on the carrying platform to match and seal the carrying platform and the flow cell. Since the sealing ring needs to be connected to the flow cell several times, a sealing reliability of the sealing ring is reduced with many usages. In some sequencing systems, an optical platform and a fluid platform of the flow cell are separated, and the flow cell needs to be transferred many times, testing the sealing reliability of the sealing ring in such use. At the same time, the reagent overflowing at an inlet or an outlet is also a potential risk of the sequencing chip. The sealing ring is easily mismatched at an end of a reagent inlet module, which affects the reagent inlet and leads a leakage of the reagent. Old sealing rings need to be replaced regularly, which increases workload of operators, and a high requirement for the professional level of the operators is also needed. During the transfer process, a clearance fit of the sealing ring may cause the reagent to leak from a junction, resulting in crystallization of the reagent at the junction and adversely affecting the sealing effect.

SUMMARY

In order to overcome some or all of the above problems and other potential problems, a flow cell and a biochemical substance reaction device using the flow cell are needed.

In a first aspect, a flow cell is provided. The flow cell includes a flow cell body, which includes a frame and a fluid chamber received in the frame. The fluid chamber includes a reaction region that allows fluid to flow through. The frame is provided with a liquid inlet, a liquid outlet, and an exhaust hole connected to the flow chamber. A fluid flows into the reaction region of the fluid chamber through the liquid inlet and flows out through the liquid outlet. The exhaust hole exhausts any gas generated in the fluid chamber when the fluid is flowing through the reaction region.

In a second aspect, a flow cell is disclosed, which includes a plurality of sealing rings. The sealing ring is positioned corresponding to a through hole connecting the flow cell to the exterior.

In a third aspect, a biochemical substance reaction device is provided, which is configured to receive the above flow cell and input a sample to the flow cell to make the sample react in the flow cell, or, the biochemical substance reaction device is further configured to detect a biometric signal of a product of the sample after reaction.

The flow cell and the biochemical substance reaction device provided by the present disclosure reduces a length to width ratio of the flow cell by setting exhaust holes on the flow cell, which allows full use of a circular wafer and realizes a rapid and effective spreading of the fluid. The flow cell is integrated with the sealing ring, which avoids an infiltration of the fluid into a substrate, permits a vacuum adsorption of the flow cell on different platforms, and avoids a reduction of sealing performance caused by a long-term use and aging of the sealing ring.

BRIEF DESCRIPTION OF THE DRAWINGS

Implementations of the present technology will now be described, by way of embodiment, with reference to the attached figures. Obviously, the drawings are only some embodiments of the present disclosure. For those of ordinary skill in the art, other drawings can be obtained based on these drawings without creative work.

Figure 1:
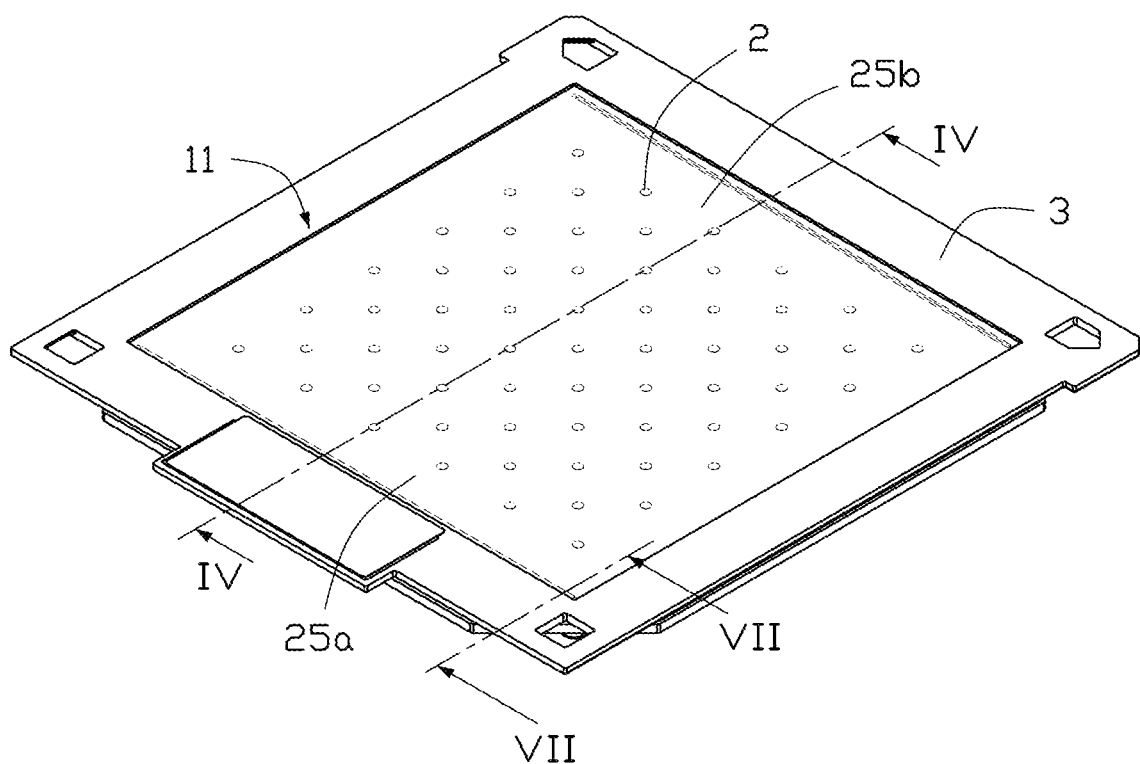
FIG. 1 is a perspective view of a flow cell according to an embodiment of the present disclosure.

Implementations of the disclosure will now be described, by way of embodiments only, with reference to the drawings.

SYMBOL DESCRIPTION OF MAIN COMPONENTS flow cell 1, 6; flow cell body 2
outer frame 3; front side 11
back side 13; sealing ring 4
frame 20; substrate 21
cover sheet 23; fluid chamber 25
glue body 26; glue body supporting point 251
liquid inlet 252; liquid outlet 253
inlet-side exhaust hole 254a; outlet-side exhaust hole 254b
inlet diversion channel 255a; outlet diversion channel 255b
bottom surface 2551a, 2551b; sidewall 2552a, 2553a, 2552b, 2553b
opening 2554a, 2554b; fixing portion 31
positioning portion 32; grabbing structure 321
corner region 322; positioning structure 323
electronic label 33; machine non-contact identification symbol 331 331
machine inductive identification element 332; character recognition symbol 333
groove 34; sealing ring fixing structure 5
fixing structure 51; fixing hole 512
ring body 41; through hole 42
clamping structure 411; bump 411a
matching structure 513; recessed portion 513a
positioning bump 514; outlet valve structure 421
valve 422; root portion 422a
top portion 422b; fluid platform 7
fluid channel 71; receiving groove 72
normally-closed valve 423; inlet end 25a
outlet end 25b; biochemical substance reaction device 8.

DETAILED DESCRIPTION

Implementations of the disclosure will now be described, by way of embodiments only, with reference to the drawings. The described embodiments are only portions of the embodiments of the present disclosure, rather than all the embodiments. The disclosure is illustrative only, and changes may be made in the detail within the principles of the present disclosure. It will, therefore, be appreciated that the embodiments may be modified within the scope of the claims.

It should be noted that when a component is referred to as being "fixed to" or "mounted on" another component, the component can be directly in contact with another component or a middle component may exist therebetween. When a component is considered to be "arranged on" another component, the component can be directly on another component or a middle component may exist therebetween. The term "and/or" as used herein means any combinations of one or more related listed items.

Figure 2:
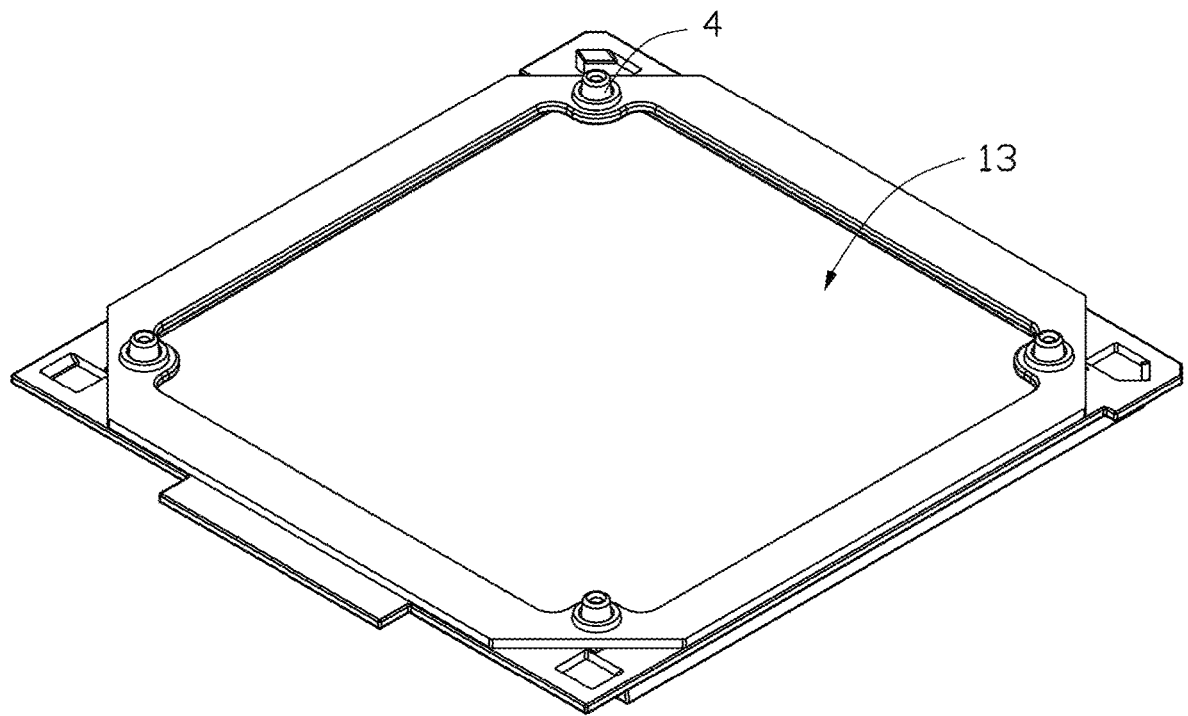
FIG. 2 is another perspective view of the flow cell of FIG. 1.
Figure 3:
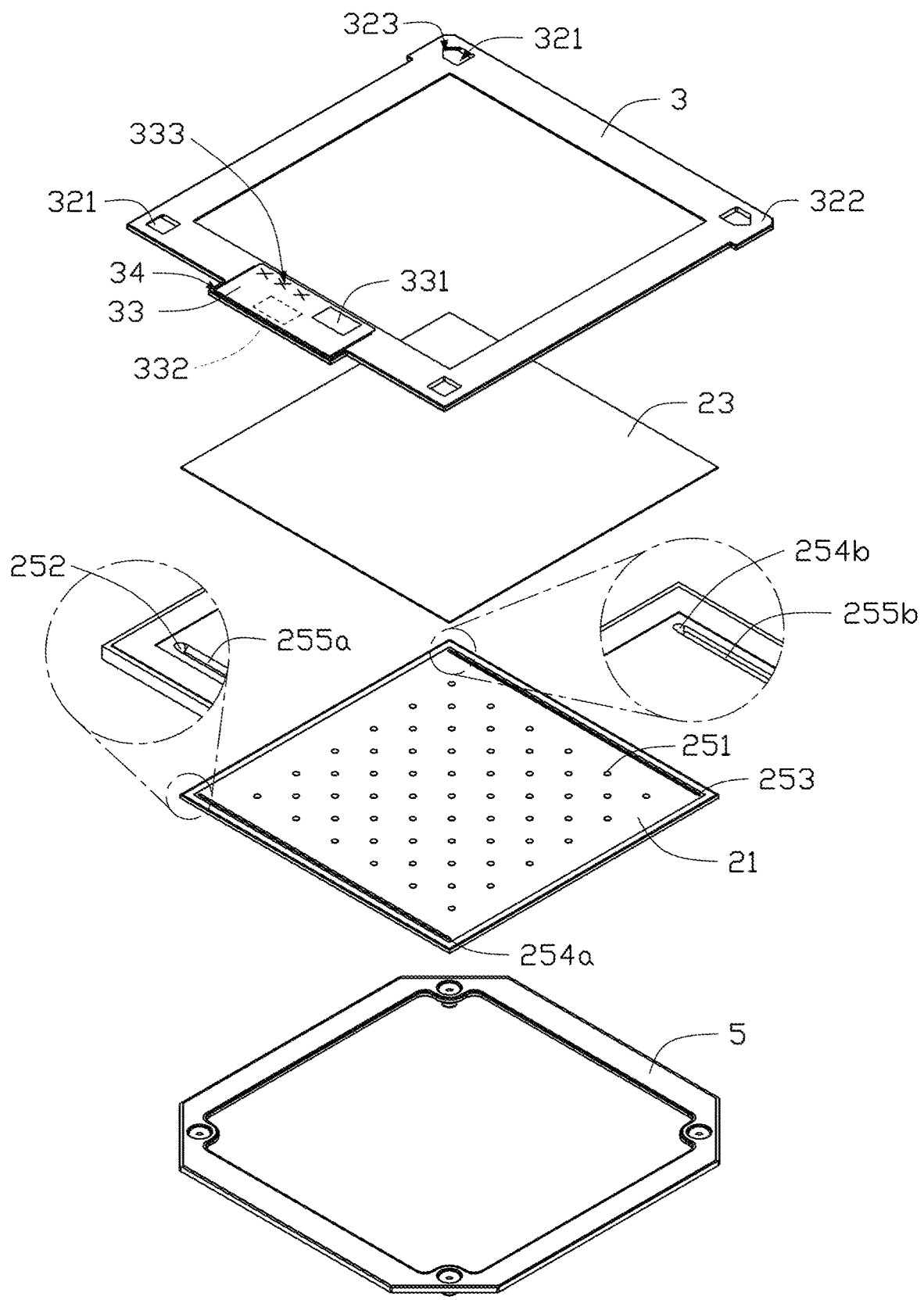
FIG. 3 is an exploded view of the flow cell of FIG. 1.

FIGS. 1 to 3 are two perspective views and an exploded view of a flow cell of the present disclosure. The flow cell 1 includes a flow cell body 2 and an outer frame 3 disposed outside of the flow cell body 2. The flow cell 1 includes a front side 11 and a back side 13 opposite to the front side 11. A plurality of sealing rings 4 are disposed on the back side 13 of the flow cell 1. The flow cell 1 can match and be sealed with different carrying platforms through the sealing rings 4. Wherein, the matching includes liquid inlet and outlet matching of the flow cell 1.

Figure 4:
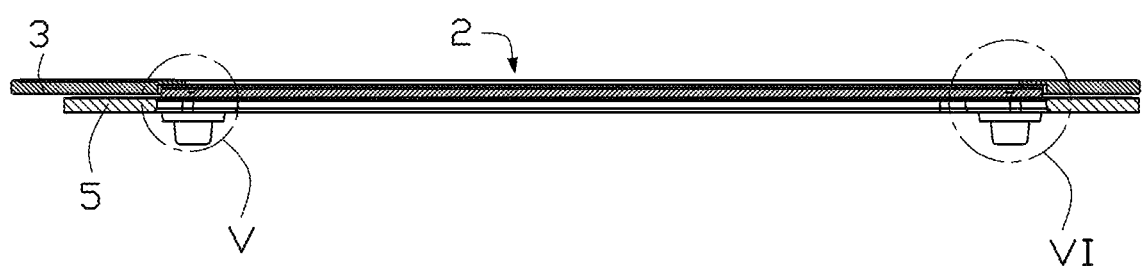
FIG. 4 is a cross-sectional view taken along line IV-IV in FIG. 1.
Figure 5:
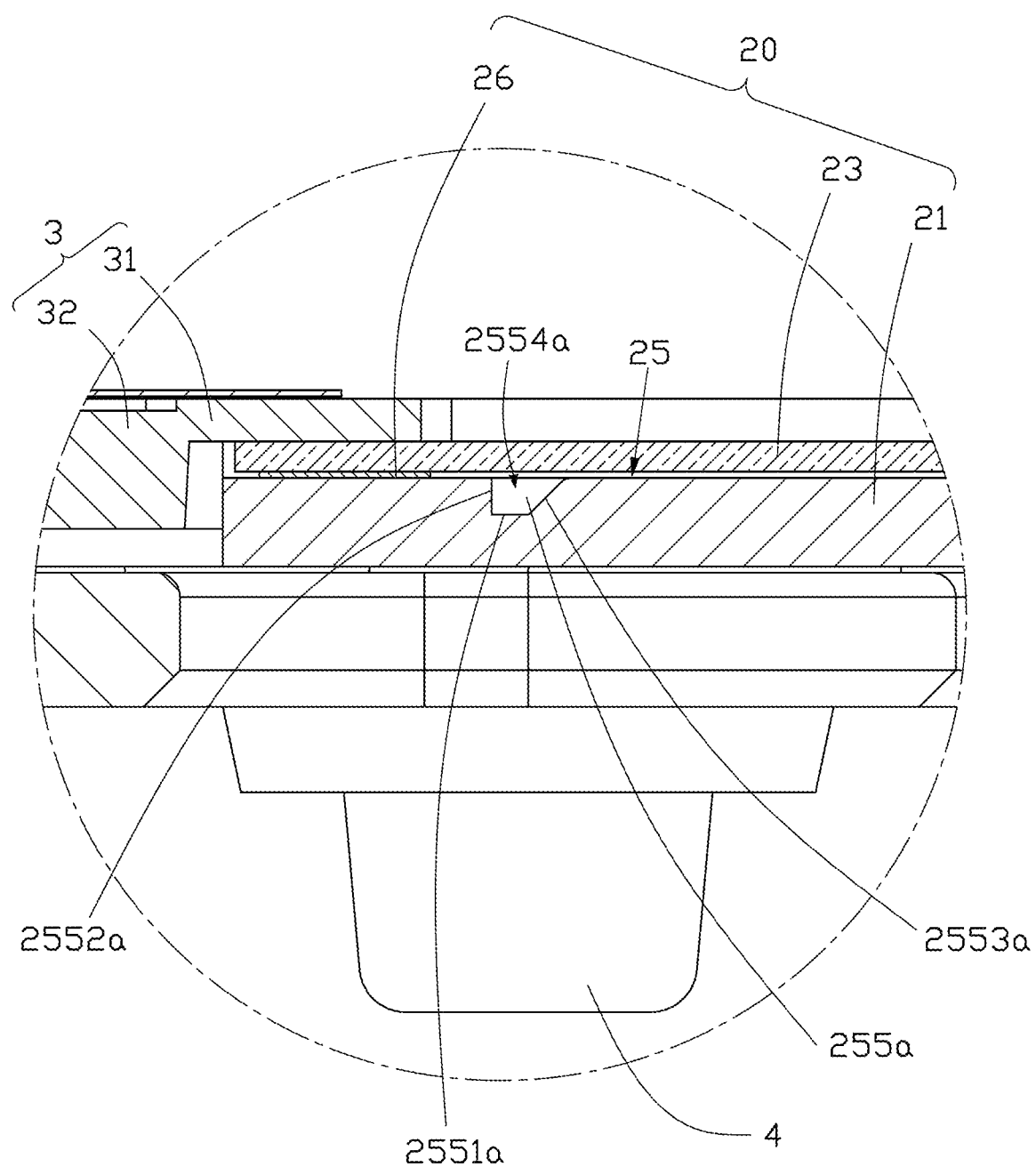
FIG. 5 is an enlarged view of region V in FIG. 4.

Referring to FIGS. 4 and 5, the flow cell body 2 includes a frame 20 and a fluid chamber 25 defined in the frame 20. The frame 20 includes a substrate 21 and a cover sheet 23 from the back side 13 to the front side 11. The cover sheet 23 allows light to pass through, so that movement of a fluid in the fluid chamber 25 can be observed on the front side 11 of the flow cell 1. In the embodiment, the cover sheet 23 is made of optical glass. The substrate 21 is a rectangular silicon wafer. Further, the substrate 21 is a rectangular silicon wafer with high-density nanolattice of gene-patterned array technology. An area around the cover sheet 23 is connected to an area around the substrate 21 through a glue body 26. The fluid chamber 25 is disposed to correspond to a central area of the cover sheet 23 and the substrate 21. In the embodiment, the glue body 26 is made of a curable glue, such as UV curing glue. The glue body 26 is continuously distributed around the area around the cover sheet 23 and the substrate 21 to form a sealing fence. The glue body 26 is mixed with microspheres of specific size or particles with shapes that can separate the cover sheet 23 and the substrate 21 by a preset distance. Thus, the cover sheet 23, the substrate 21, and the glue body 23 cooperate to form the fluid chamber 25 corresponding to the central area of the cover 23 and the substrate 21. A periphery of the fluid chamber 25 is sealed by the glue body 26 to form a closed reaction chamber in which the fluid reacts with a sample.

In the embodiment, the flow cell 1 is substantially rectangular or square. The flow cell body 2 is substantially rectangular or square. The frame 20 is substantially rectangular or square. The fluid chamber 25 is also substantially rectangular or square. In other embodiments, the flow cell 1, the flow cell body 2, the frame 20, and/or the fluid chamber 25 may be also other shapes.

Referring to FIGS. 1 and 3, supporting points are disposed in the flow chamber 25. In the embodiment, the supporting points are glue body supporting points 251. Two ends of each glue body supporting point 251 are connected to and support the cover sheet 23 and the substrate 21, respectively, so as to improve an inner structural strength of the flow cell body 2. In the embodiment, the glue body supporting point 251 is also made of UV curing glue. The glue body supporting point 251 is also mixed with microspheres of specific size or particles with shapes that can separate the cover sheet 23 and the substrate 21 by a preset distance. In the embodiment, a plurality of glue body supporting points 251 is disposed in the flow chamber 25, and the glue body supporting points 251 are disposed at intervals.

In the embodiment, the substrate 21 may be made of optical glass, fused quartz, monocrystalline silicon sheet, polycrystalline silicon sheet, or other ceramic materials. A diameter of the microsphere is any value in a range of 30 microns to 80 microns.

At the back side 13 of the flow cell 1, a liquid inlet 252, a liquid outlet 253, and two exhaust holes 254a (and 254b) are defined on the substrate 21. In the embodiment, the liquid inlet 252 and the liquid outlet 253 are disposed on a diagonal line through the fluid chamber 25. The exhaust hole 254a (hereinafter, "inlet-side exhaust hole 254a") is disposed on the same side as the liquid inlet 252. A diversion channel 255a (hereinafter, "inlet diversion channel 255a") is connected between the liquid inlet 252 and the inlet-side exhaust hole 254a. The exhaust hole 254b (hereinafter, "outlet-side exhaust hole 254b") is disposed on the same side as the liquid outlet 253. The liquid outlet 253 is connected to the outlet-side exhaust hole 254b through a diversion channel 255b (hereinafter, "outlet diversion channel 255b"). In the embodiment, the inlet diversion channel 255a and the outlet diversion channel 255b are respectively disposed on opposite sides of the fluid chamber 25. The inlet diversion channel 255a and the outlet diversion channel 255b are substantially parallel with each other. In the embodiment, the inlet-side exhaust hole 254a and the outlet-side exhaust hole 254b are disposed on another diagonal line through the fluid chamber 25.

Figure 6:
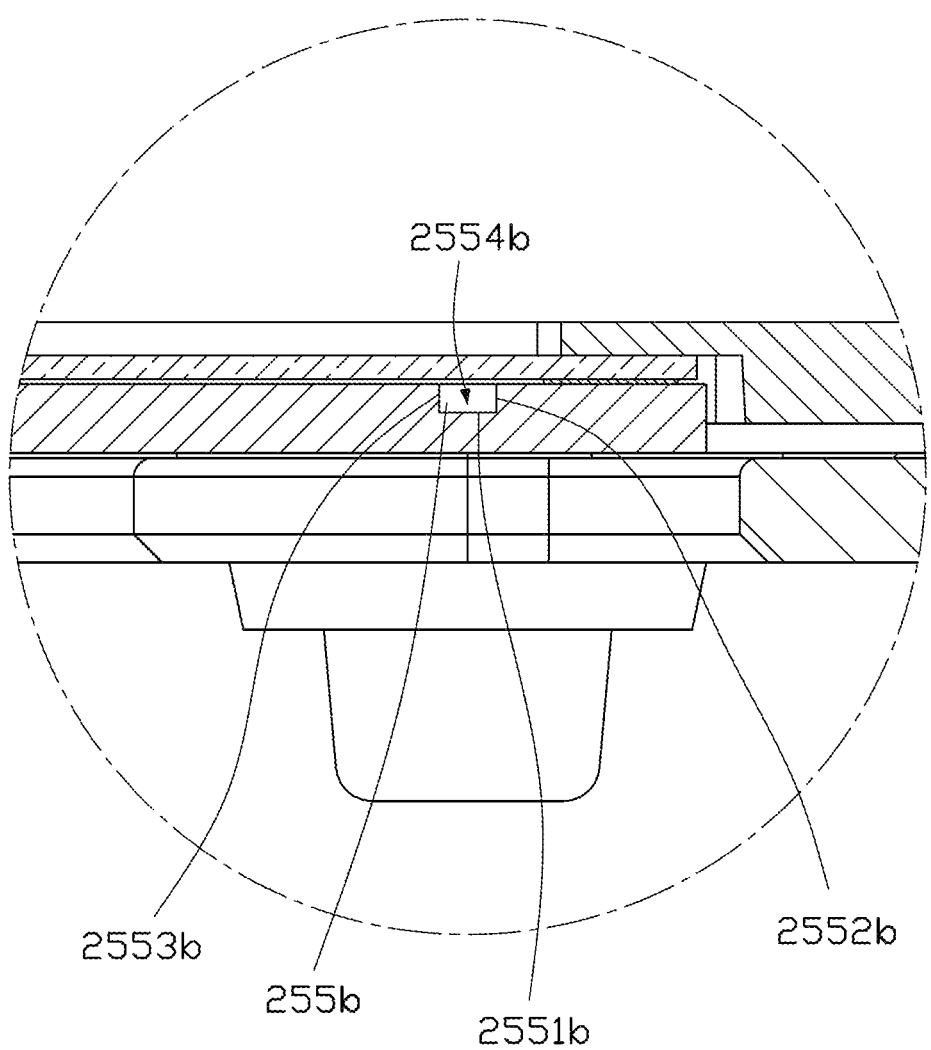
FIG. 6 is an enlarged view of region VI in FIG. 4.

Referring to FIGS. 4 to 6, the inlet diversion channel 255a includes a bottom surface 2551a, a sidewall 2552a, another sidewall 2553a, and an opening 2554a. The opening 2554a is opposite to the bottom surface 2551a. The inlet diversion channel 255a is connected to the fluid chamber 25 through the opening 2554a. The sidewalls 2552a (and 2553a) are disposed and connected between the opening 2554a and the bottom surface 2551a. The sidewall 2553a is closer than the sidewall 2552a to a middle area of the fluid chamber 25. In the embodiment, the sidewall 2552a is substantially perpendicular to the bottom surface 2551a and the opening 2554a. The sidewall 2553a is an inclined wall, which is inclined to the bottom surface 2551a and the opening 2554a. The sidewall 2553a starts from the bottom surface 2551a and extends upward to the middle area of the fluid chamber 25, so that a top of the sidewall 2553a is closer than the bottom of the sidewall 2553a to the middle area of the fluid chamber 25. In the embodiment, a connecting portion of the top of the sidewall 2553a connected to a surface of the substrate 21 has a substantially rounded corner, so that the sidewall 2553a extends smoothly to the substrate 21. The opening 2554a of the inlet diversion channel 255a is expanded when one sidewall of the inlet diversion channel 255a is inclined. When the sidewall 2553a merges smoothly to the substrate 21, any fluid disturbance near the liquid inlet 252 is avoided, risk of a vortex is reduced, and uniformity of biochemical reaction near the liquid inlet 252 is improved.

After entering the fluid chamber 25 from the liquid inlet 252, fluid flows along the inlet diversion channel 255a to the inlet-side exhaust hole 254a. With the increase of the fluid in the fluid chamber 25, the fluid flows from an inlet end 25a where the liquid inlet 252 and the inlet diversion channel 255a are located, to an outlet end 25b where the liquid outlet 253 and the outlet diversion channel 255b are located, then flows into the outlet diversion channel 255b. The fluid further flows to the liquid outlet 253 guided by the outlet diversion channel 255b, and finally flows out of the flow chamber 25 through the liquid outlet 253. Through the exhaust holes 254a and 254b and the diversion channels 255a and 255b arranged in the flow cell 1, the fluid is evenly spread over the fluid chamber 25 to allow the fluid flowing through all possible regions (reaction regions), so as to ensure the uniformity of biochemical reaction in the fluid chamber 25.

In other embodiments, the sidewall 2552a is also an inclined plane. A top of the sidewall 2552a near the opening 2554a is closer than the bottom of the sidewall 2552a to an edge area of the fluid chamber 25.

The outlet diversion channel 255b is connected between the liquid outlet 253 and the outlet-side exhaust hole 254b. The outlet diversion channel 255b includes a bottom surface 2551b, two sidewalls 2552b and 2553b, and an opening 2554b. The opening 2554b is opposite to the bottom surface 2551b. The outlet diversion channel 255b is connected to the fluid chamber 25 through the opening 2554b. The sidewalls 2552b and 2553b are connected between the opening 2554b and the bottom surface 2551b. In the embodiment, the sidewalls 2552b and 2553b are substantially perpendicular to the bottom surface 2551b and the opening 2554b. In other embodiments, at least one of the sidewalls 2552b 2553b may be inclined. For example, the outlet diversion channel 255b may be disposed symmetrically with the inlet diversion channel 255a.

Referring to FIGS. 3, 5 and 6, the outer frame 3 surrounds the peripheral sides of the flow cell body 2. The outer frame 3 includes a fixing portion 31 and a positioning portion 32. The fixing portion 31 is disposed on an inner side of the positioning portion 32. The fixing portion 31 fixes the outer frame 3 on the cover sheet 23. In the embodiment, the fixing portion 31 is bonded to a surrounding area of the cover sheet 23 by glue. The positioning portion 32 is disposed outside of the fixing portion 31. A thickness of the fixing portion 31 is thinner than that of the positioning portion 32. Problems of interference with an optical scanning system may be avoided when the thickness of the fixing portion 31 is ultra-thin. The positioning portion 32 protrudes towards the back side 13 of the flow cell 1 compared with the fixing portion 31. A side of the fixing portion 31 facing the back side 13 of the flow cell 1 is bonded to the surrounding area of the cover sheet 23, so as to fix the outer frame 3 on the cover sheet 23. The positioning portion 32 includes a plurality of grabbing structures 321. The grabbing structures 321 are used to grab and move the flow cell 1 in, or to and from, different positions under a control of a mobile device (not shown). For example, when the flow cell 1 is used for gene sequencing, the flow cell 1 needs to be moved repeatedly between a fluid reaction area and an optical photographing area. At this time, the mobile device can control the grabbing structures 321 on the positioning portion 32 to move the flow cell 1 repeatedly between the fluid reaction area and the optical photographing area. In the embodiment, the grabbing structures 321 are holes defined on the positioning portion 32. In the embodiment, the grabbing structures 321 are rectangular holes defined on four corner regions 322 of the positioning portion 32. In other embodiment, the grabbing structures 321 may be holes of other shapes, such as circular holes. The grabbing structures 321 may be disposed at other positions of the positioning portion 32. The positioning portion 32 further includes a positioning structure 323, which used to position the flow cell 1 when the mobile device moves and places the flow cell 1 on the carrying platform, so as to ensure accurate placement of the flow cell 1 on the carrying platforms. In the embodiment, the positioning structure 323 is a V-shaped inclined slot hole. In the embodiment, there are two positioning structures 323, and each positioning structure 323 is a V-shaped inclined slot hole. In the embodiment, each V-shaped inclined slot hole is disposed on one side of each hole as the grabbing structure 321 and connected to the hole. In other embodiments, the positioning structures 323 may be integrated with the grabbing structures 321, that is, one positioning portion 32 can be used to taking hold of and positioning the flow cell 1. For example, some holes with azimuth pointing features, such as triangles, can be used as the positioning structure 323 and the grabbing structure 321 at the same time. In the embodiment, the positioning portion 32 surrounds the outsides of the cover sheet 23 and the substrate 21 of the flow cell 1 to protect the flow cell 1. In the embodiment, the outer frame 3 is formed by injection molding. The outer frame 3 may be made of glass fiber, carbon fiber reinforced polymer plastic, or other common plastic.

One side of the outer frame 3 facing the front side 11 of the flow cell 1 includes an electronic label 33. In the embodiment, the electronic label 33 is pasted on the outer frame 3. The electronic label 33 includes not only a non-contact machine identification symbol 331 disposed outside the electronic label 33, but also a machine induction identification element 332 disposed inside the electronic label 33. The electronic label 33 further includes a character recognition symbol 333. In the embodiment, the non-contact machine identification symbol 331 may be an optically-readable identification symbol such as one-dimensional code and two-dimensional code, etc. The machine inductive identification element 332 may be an RFID (radio frequency identification) module.

A position where the electronic label 33 is disposed on the outer frame 3 is recessed downward to form a groove 34, and the electronic label 33 is received in the groove 34, so as to avoid the electronic label 33 being elevated a surface of the outer frame 3 and interfering with other components.

Figure 7:
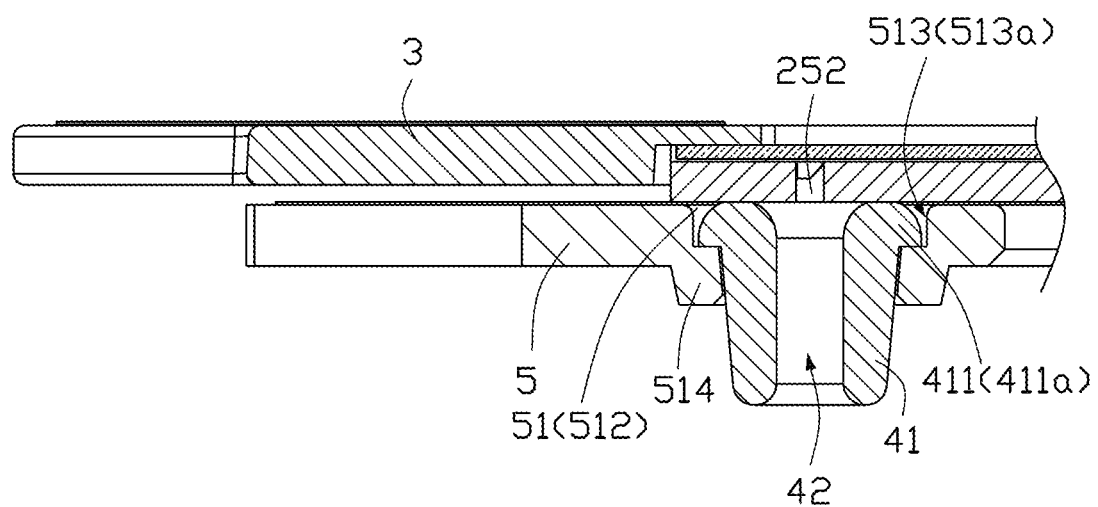
FIG. 7 is a partial cross-sectional view taken along line VII-VII in FIG. 1.
Figure 8:
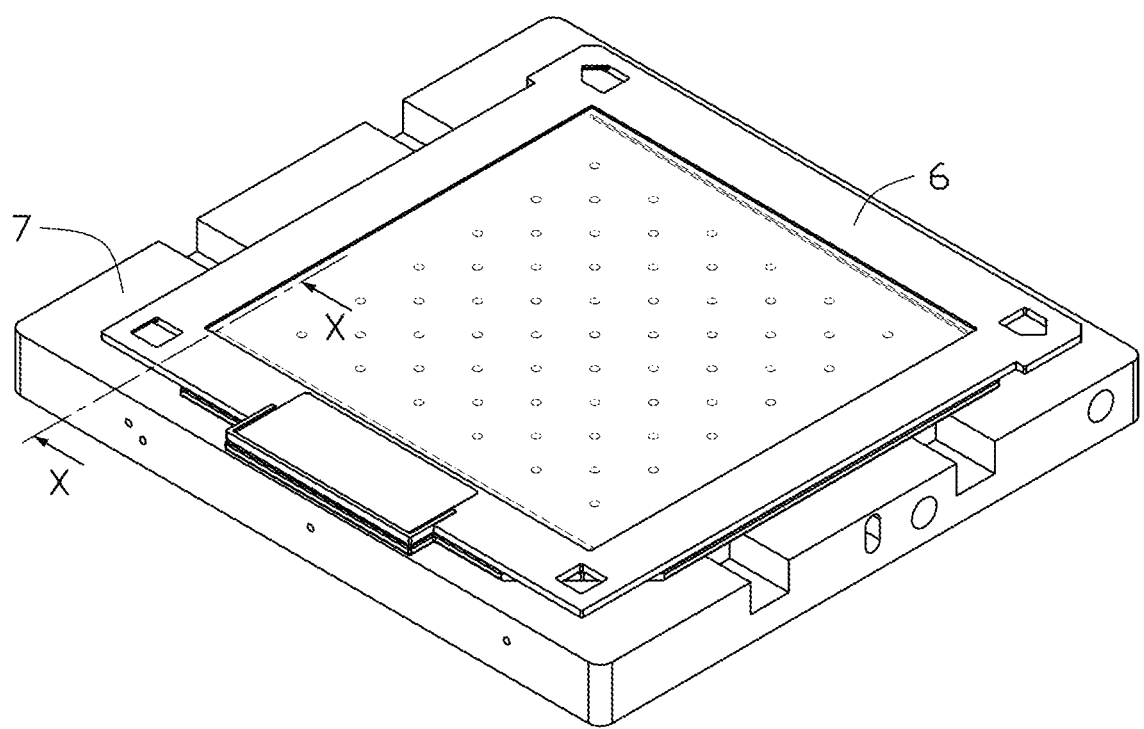
FIG. 8 is a diagrammatic view showing another flow cell disposed in a carrying platform according to an embodiment of the present disclosure.
Figure 9:
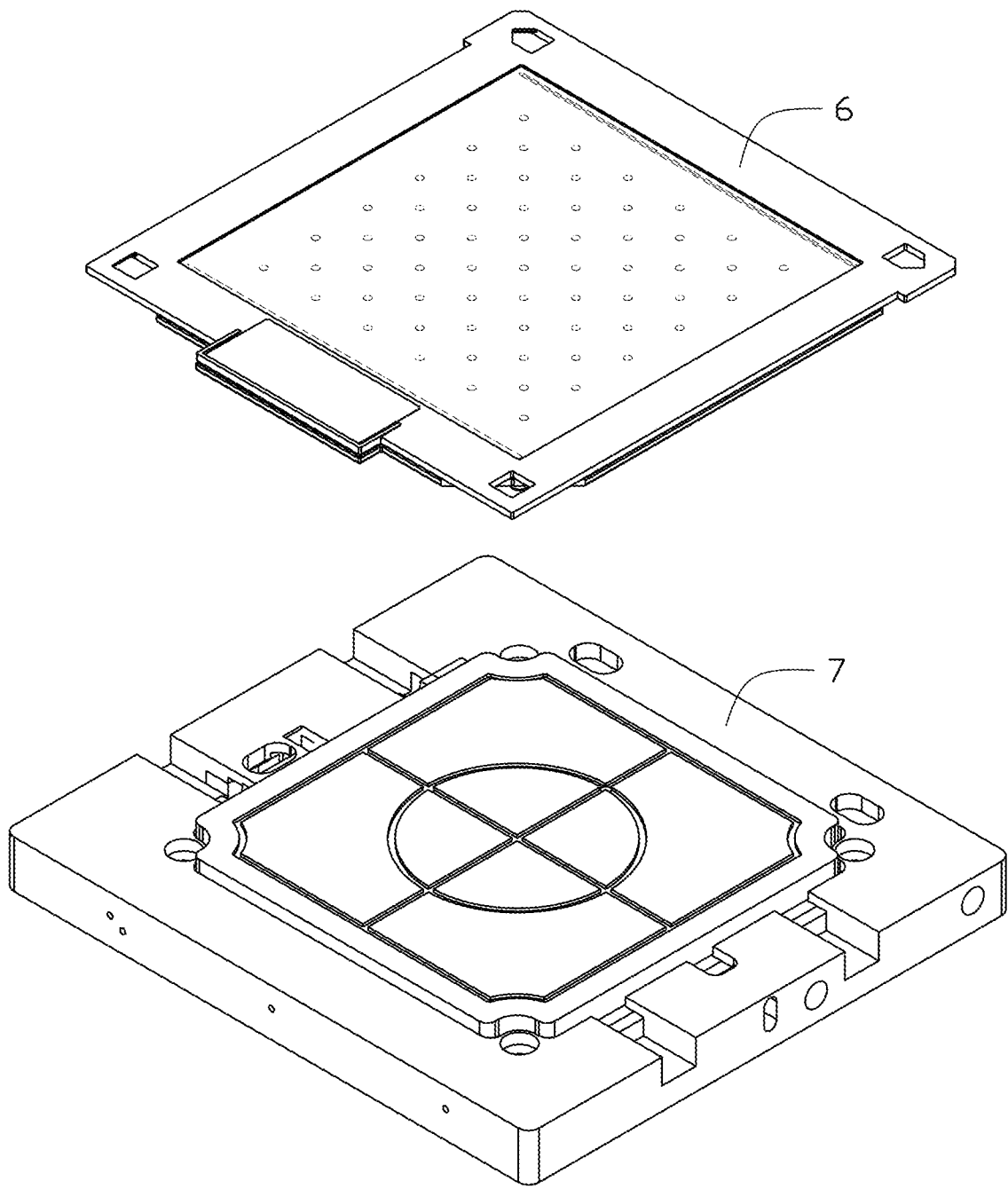
FIG. 9 is a diagrammatic view showing the flow cell separated from the carrying platform in FIG. 8.

Referring to FIGS. 2, 3, and 7, a plurality of sealing rings 4 is disposed on the back side 13 of the flow cell 1. The sealing rings 4 are disposed corresponding to the liquid inlet 252, the liquid outlet 253, and the exhaust holes 254a and 254b, respectively. The flow cell 1 can be matched and sealed with different carrying platforms through the sealing rings 4.

The sealing ring 4 is fixed on the back side 13 of the flow cell 1 through a sealing ring fixing structure 5. In the embodiment, the sealing ring fixing structure 5 is a rectangular frame. Four fixing structures 51 are disposed on the rectangular frame corresponding to the liquid inlet 252, liquid outlet 253, and the two exhaust holes 254a and 254b, respectively. The sealing ring 4 is fixed on the flow cell 1 through the fixing structure 51. In the embodiment, the fixing structure 51 is a fixing hole 512. The sealing ring 4 is installed in the fixing hole 512. Each sealing ring 4 includes a ring body 41. The ring body 41 defines a through hole 42. The through hole 42 may be cylindrical or conical. At least one clamping structure 411 matched with an inner structure of the fixing hole 512 is disposed on the ring body 41. The clamping structure 411 is embedded in the fixing hole 512 to match with the inner structure of the fixing hole 512. In the embodiment, the clamping structure 411 of each sealing ring 4 is a bump 411a disposed on outside of the ring body 41. A matching structure 513 is disposed in the fixing hole 512 of each sealing ring 4. The matching structure 513 cooperates with the clamping structure 411 of the sealing ring 4 to fix the sealing ring 4 in the fixing hole 512. In the embodiment, the matching structure 513 of each fixing hole 512 is a recessed portion 513a defined in the fixing hole 512. The bump 411a of the sealing ring 4 is received in the recessed portion 513a to secure the sealing ring 4 in the fixing hole 512.

Understandably, in other embodiments, the clamping structure 411 of the sealing ring 4 may be a recessed portion defined on the ring body 41. A matching structure in the fixing hole 512 may be a bump disposed in the fixing hole 512. Understandably, in other embodiments, the clamping structure 411 of the sealing ring 4 may be an outer surface of the ring body 41, and the matching structure in the fixing hole 512 may be an inner surface of the fixing hole 512. The sealing ring 4 is fixed in the fixing hole 512 through an interference fit between the outer surface of the sealing ring 4 and the inner surface of the fixing hole 512. Understandably, in other embodiments, the sealing ring 4 may be fixed in the fixing hole 512 by adhesive.

In the embodiment, a positioning bump 514 is disposed on each fixing hole 512. After being fixed in the fixing hole 512, one end of the sealing ring 4 extends out from the positioning bump 514, so that the positioning bump 514 is sleeved outside of the sealing ring 4. The positioning bump 514 cooperates with the corresponding portion on the carrying platform (such as the liquid inlets and outlets on the fluid platform) to assist in positioning the flow cell 1 and avoid the fluid flow being affected by deformation of the sealing ring 4.

In the embodiment, the sealing ring fixing structure 5 is fixed on the back side 13 of the flow cell 1. In the embodiment, the sealing ring fixing structure 5 is pasted on the back side 13 of the flow cell 1 through glue, such as double-sided adhesive. In the embodiment, the sealing rings 4 are simultaneously fixed on the back side 13 of the flow cell 1 through one sealing ring fixing structure 5. In other embodiments, the sealing ring fixing structure 5 can be divided into a plurality of independent sub fixing structures, and each sub fixing structure fixes one sealing ring 4.

Figure 10:
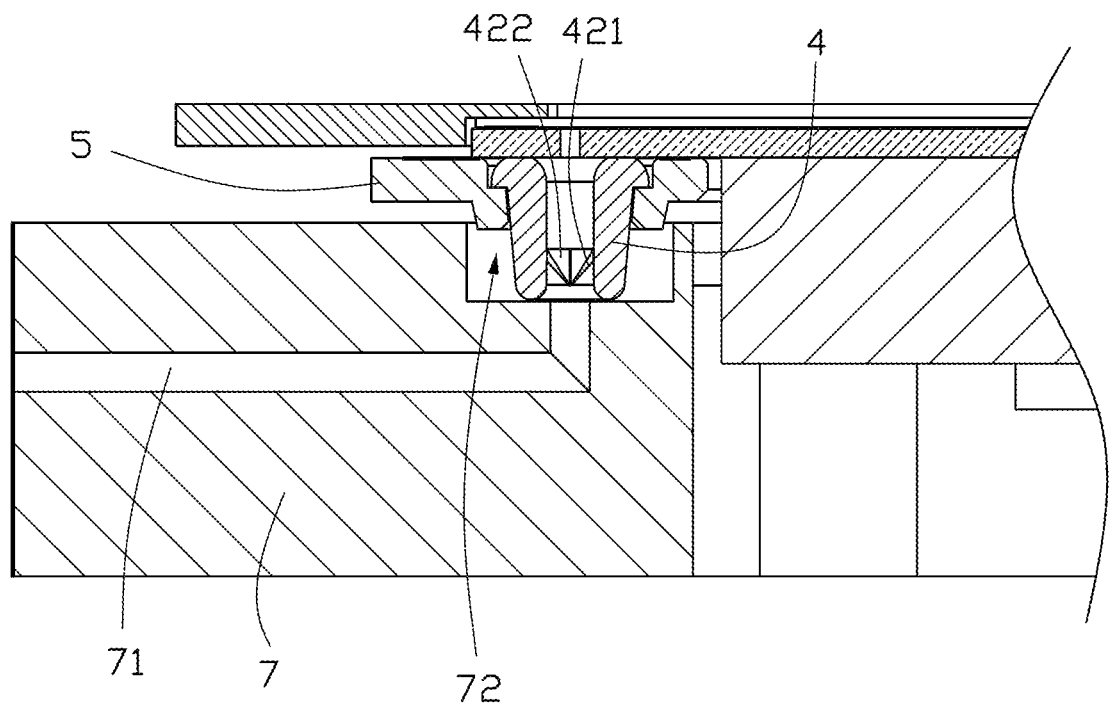
FIG. 10 is a partial cross-sectional view taken along line X-X in FIG. 8.
Figure 11:
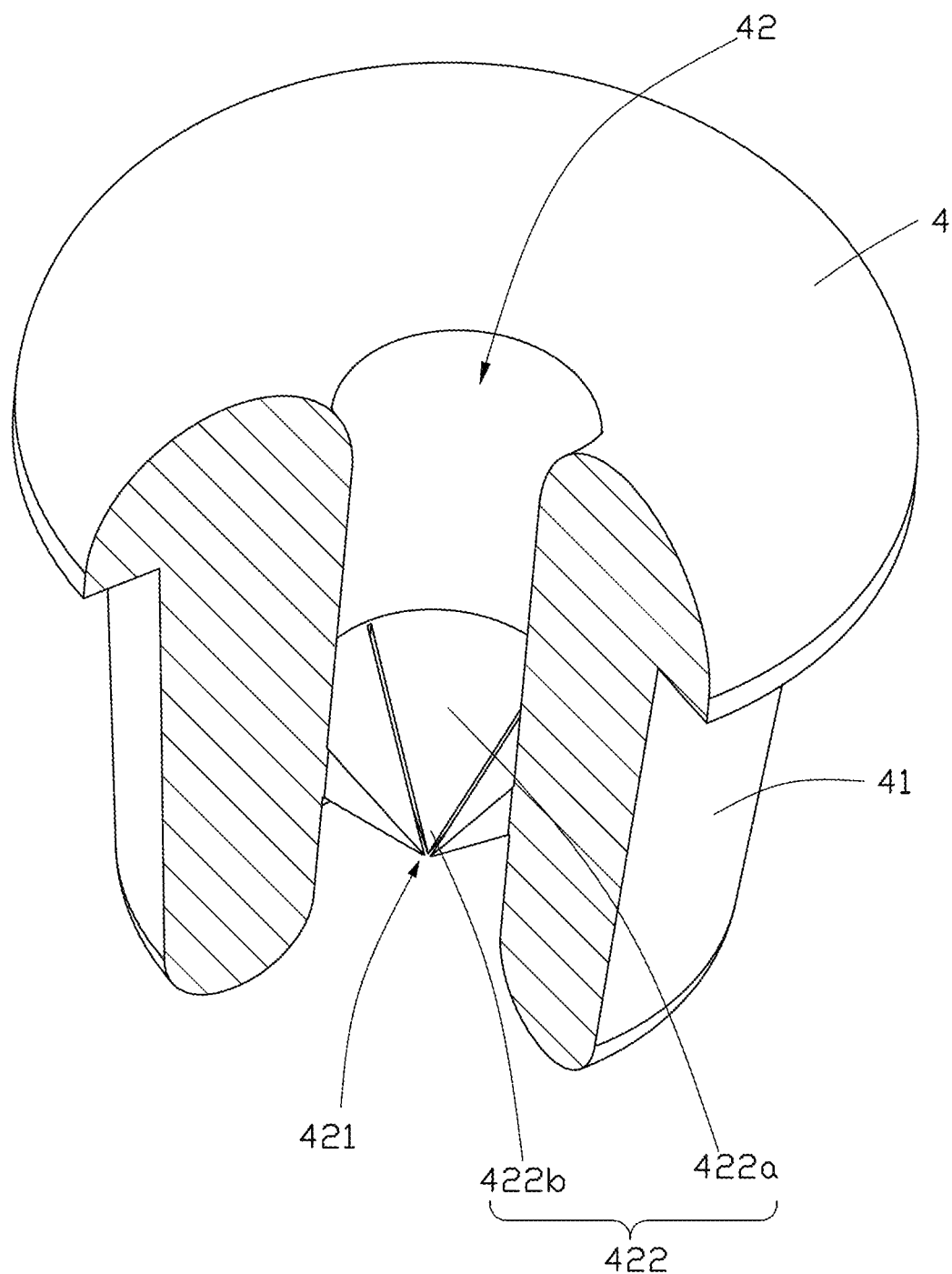
FIG. 11 is a partial cross-sectional view of a sealing ring disposed on a liquid outlet of the flow cell in FIG. 8.

Referring to FIGS. 8 to 11, are diagrammatic views showing the flow cell disposed in a carrying platform according to another embodiment of the present disclosure. A structure of the flow cell 6 is basically same as that of the flow cell 1 in the previous embodiment. The main differences between the flow cell 6 and the flow cell 1 are that a unidirectional sealing structure is disposed in the through hole 42 of the sealing ring 4 in the flow cell 6. In the embodiment, the unidirectional sealing structure is a valve structure. Wherein, a liquid inlet valve structure is disposed in the through hole 42 of the sealing ring 4 corresponding to the liquid inlet 252. A liquid outlet valve structure 421 is disposed in the through hole 42 corresponding to the liquid outlet 253 and the exhaust holes 254a (and 254b). FIG. 10 shows one of the liquid outlet valve structures 421. In the embodiment, the liquid outlet valve structure 421 includes a plurality of valves 422. Each valve 422 includes a root portion 422a and a top portion 422b. The root portion 422a is connected to a hole wall of the through hole 42. The top portion 422b extends out from the root portion 422a to the center and outside of the through hole 42. The liquid outlet valve structure 421 is conical or approximately conical with the top end facing an outside of the through hole 42. The root portions 422a of all valves 422 are connected with each other in turn, or the root portions 422a of all valves 422 are separated from each other, and the separated root portions 422a are close to each other. The top portions 422b of all valves 422 are separated from each other, and the separated top portions 422b are surrounded together to form a sealing structure that only allows a one-way flow of the fluid in the flow cell 6. The liquid inlet valve structure is not shown in FIG. 10. A principle of the liquid inlet valve structure is the same as that of the liquid outlet valve structure 421. The liquid inlet valve structure only allows a unidirectional flow of the fluid in the flow cell 6 from the liquid inlet 252 to the liquid outlet 253. A structure of the liquid inlet valve structure is similar to that of the liquid outlet valve structure 421 except that the top of the liquid inlet valve of the liquid inlet valve structure extends from the root to the center and inner side of the through hole 42. Thus, the liquid inlet valve structure is conical or approximately conical with the top facing the inside of the through hole 42.

Referring to FIG. 10, In the embodiment, the carrying platform is a fluid platform 7. The fluid platform 7 includes fluid channels 71 corresponding to the liquid inlet 252, the liquid outlet 253, and the exhaust holes 254a and 254b of the flow cell 6. A receiving groove 72 is defined in the fluid platform 7. The receiving groove 72 corresponds to connecting portions between the fluid channel 71 and the liquid inlet 252, the liquid outlet 253, or the exhaust holes 254a and 254b. After the flow cell 6 is installed on the fluid platform 7, the positioning bumps 514 and the sealing rings 4 extend into the receiving groove 72. The ends of the sealing rings 4 press against the bottom of the receiving groove 72, and the through hole 42 in the sealing ring 4 connects to the flow channel 71. Thus, a fluid channel is formed between the flow cell 6 and the fluid platform 7.

Figure 12:
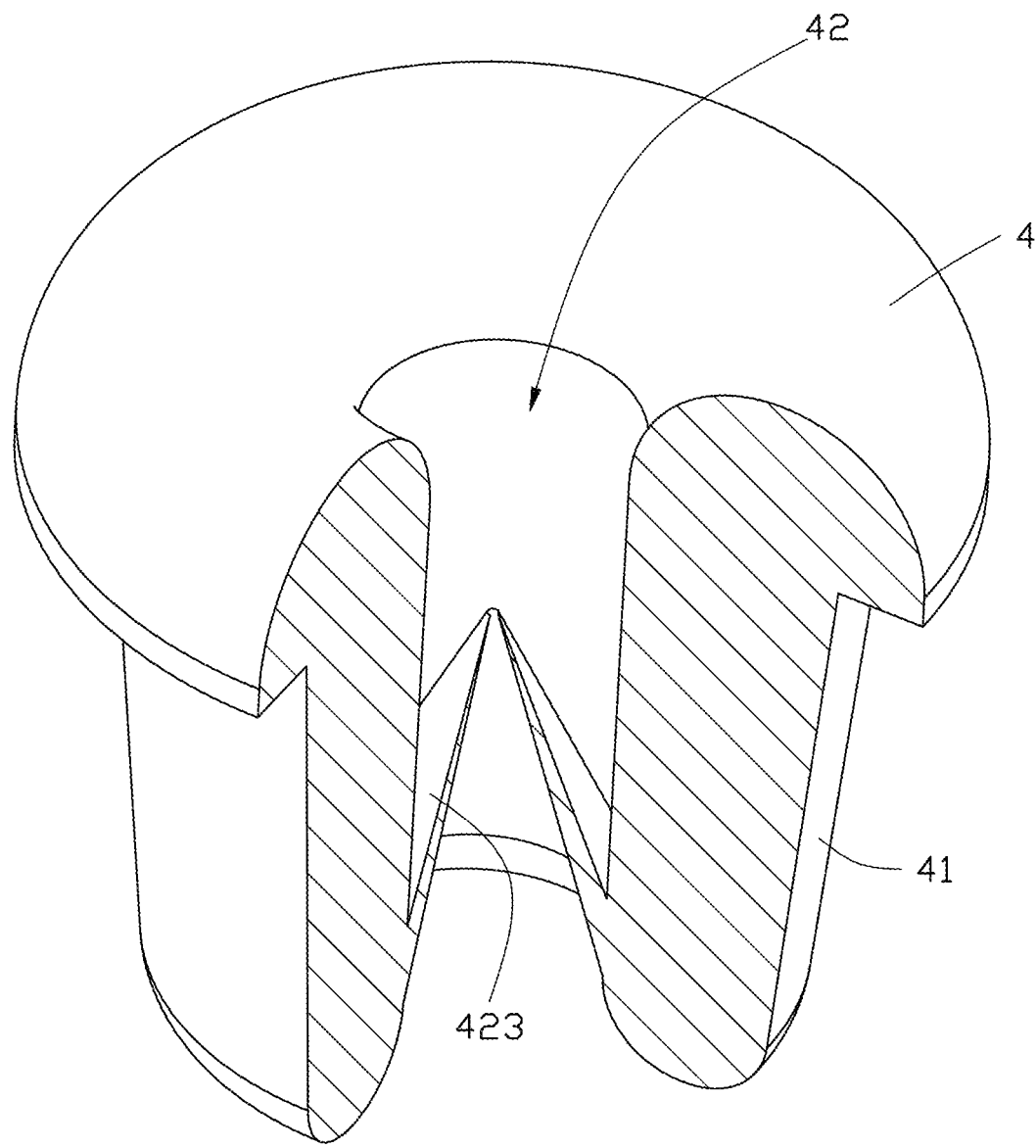
FIG. 12 is a partial cross-sectional view of a sealing ring according to another embodiment of the present disclosure.

FIG. 12 is a partial sectional view of another sealing ring 4. The sealing ring 4 includes a ring body 41, a through hole 42 surrounded by the ring body 41, and a sealing structure disposed in the through hole 42. In the embodiment, the sealing structure is a normally-closed valve 423. A root of the normally-closed valve 423 is connected to a wall of the through hole 42 to close the through hole 42, so that the sealing ring 4 in the flow cell remains completely closed before assembly on the fluid platform, to effectively avoid overflow of the fluid after the flow cell is separated from the fluid platform. After assembly on the fluid platform, the normally-closed valve 423 is punctured by a liquid inlet/outlet needle to allow communication and passage between the flow cell and the flow channel of the fluid platform.

Figure 13:
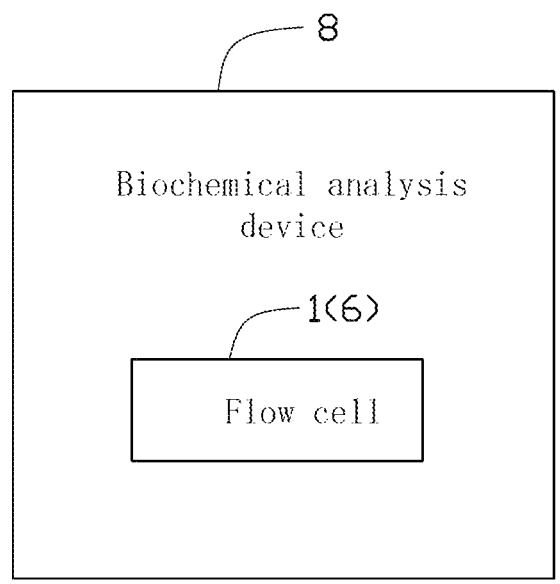
FIG. 13 is a diagrammatic view of a biochemical substance reaction device according to an embodiment of the present disclosure.

FIG. 13 is a biochemical substance reaction device 8 using the flow cell 1 (6), which is used to carry the flow cell and input a reactive sample into the flow cell to undergo a reaction in the flow cell. Or, the biochemical substance reaction device is further used to detect a product obtained from the reaction of the sample to obtain a signal reflecting biological characteristics of the product. The biochemical substance reaction device 8 may be a gene sequencer, a liquid chromatograph, a biochemical analyzer, and a medical device, etc.

In sum, the flow cell provided by the embodiments of the present disclosure includes the flow cell body. The flow cell body includes the frame and the fluid chamber defined in the flow cell body. The fluid chamber defines a fluid channel and includes a reaction region to allow the fluid to flow through. The liquid inlet and the liquid outlet connected to the fluid chamber are defined in the frame. The fluid inputted from the liquid inlet flows through the reaction region in the fluid chamber and flows out through the liquid outlet.

In sum, the flow cell is provided by the embodiments of the present disclosure. The liquid inlet, the liquid outlet, and the exhaust holes are defined on the frame, which are connected to the fluid chamber. The fluid inputted from the liquid inlet flows through the reaction region in the fluid chamber and flows out through the liquid outlet. The exhaust holes discharge any gas generated in the fluid chamber during the fluid flow through the reaction region.

In sum, the flow cell is provided by the embodiments of the present disclosure. The exhaust holes include the inlet-side exhaust hole. The inlet diversion channel is connected between the inlet-side exhaust hole and the liquid inlet. The exhaust hole includes the outlet-side exhaust hole. The outlet diversion channel is connected between the outlet-side exhaust hole and the liquid outlet. Each of the inlet diversion channel and the outlet diversion channel includes the opening connected to the fluid chamber. Through the exhaust holes and the diversion channels arranged in the flow cell, the fluid is evenly spread over the fluid chamber to allow the fluid to flow through all possible flow regions (reaction regions), so as to ensure the uniformity of biochemical reaction in the fluid chamber.

Further, the inlet diversion channel and the outlet diversion channel are all defined in the frame. The inlet diversion channel is connected between two sidewalls of the liquid inlet and inlet-side exhaust hole. The sidewall close to the middle area of the fluid chamber is inclined towards the middle area. The connecting portion of the inclined sidewall connected to the opening of the inlet diversion channel has a corner which is substantially rounded. Through the inclined sidewall and/or the connecting portion with a rounded corner, fluid disturbance near the liquid inlet is avoided, vortexes under high-speed flow are weakened, and uniformity of biochemical reaction near the liquid inlet is improved.

The flow cell is provided by the embodiments of the present disclosure. A supporting point is disposed in the flow chamber. Further, a plurality of supporting points is disposed in the flow chamber, and the supporting points are disposed at intervals, so as to improve the inner structural strength of the flow cell. Further, the supporting points are glue body supporting points. The glue body supporting point is mixed with microspheres of specific size or particles to support the flow cell.

The flow cell is provided by the embodiments of the present disclosure. The frame of the flow cell includes the substrate, the cover sheet, and the sealing fence connected and sealing the substrate and the cover sheet. The substrate, the cover sheet, and the sealing fence cooperate to form the fluid chamber. The sealing fence is a glue body. The glue body is mixed with microspheres of specific size or particles with shapes that can separate the cover sheet and the substrate by a preset distance to form the fluid chamber. The support points and sealing fence are formed by the glue mixed with microspheres of specific size or particles. The high-precision structural packaging of flow cell can be completed through a dispensing machine and tooling. The micron level height of the flow cell can be controlled through the height of the particle or the diameter of the microsphere.

The flow cell is provided by the embodiments of the present disclosure. The flow cell body is rectangular or square, the liquid inlet and the liquid outlet are disposed on a diagonal line through the flow cell body, and two exhaust holes are disposed on another diagonal line through the flow cell body. The flow cell body is cut into rectangles or even squares, which maximizes the wafer area. Through the addition of two exhaust holes, positive pressure can be used to pump the reagent into the flow cell and uniformly spread the reagent on the substrate surface for biochemical reaction. At the same time, compared with negative pressure pumping, the positive pressure pumping has faster reagent flowing speed, shorter reagent replacement time, and less reagent replacement ratio.

The flow cell is provided by the embodiments of the present disclosure. The flow cell further includes the outside frame, which is used to allow the mobile device to move the flow cell. Further, the outside frame includes grabbing structures. The grabbing structure is a hole defined in the outside frame. The outside frame further positions the flow cell when the mobile device moves and places the flow cell on the carrying platform. The outside frame further includes the positioning structure. The positioning structure is a hole with azimuth pointing characteristics defined in the outside frame. Further, the grabbing structure and the positioning structure are the same structure. Further, the outer frame includes the fixing portion and the positioning portion. The fixing portion is bonded in the cover sheet. The thickness of the fixing portion is thinner than that of the positioning portion. Problems of interference with an optical scanning system are avoided when the thickness of the fixing portion is ultra-thin. Comparing with the fixing portion, the positioning portion protrudes towards the back side of the flow cell to save the flow cell during moving and positioning the flow cell. The outer frame is formed by high-precision injection molding, which maintains a low cost, at the same time, effectively fixes and protects the flow cell body, and provides supporting grabbing points for the mobile device to move the flow cell. The fixing portion with ultra-thin thickness avoids the interference of the optical scanning system.

The flow cell is provided by the embodiments of the present disclosure. The flow cell further includes the electronic label disposed on the outside frame. The electronic label not only provides information of the flow cell to the naked eye, but also provides information of the flow cell which is electronically readable, which reduces manual operation and avoids human errors.

The flow cell is provided by the embodiments of the present disclosure. The flow cell further includes the sealing rings disposed on the back side of the flow cell. The sealing rings match with and seal the flow cell to different carrying platforms. The integrated setting of sealing rings and flow cell can effectively avoid the influence of fluid infiltration of the substrate on the vacuum adsorption of flow cell on different platforms and also avoids reduction of the sealing performance caused by the long-term use and aging of the sealing rings. The sealing rings are disposed to correspond to the liquid inlet and the liquid outlet. The sealing rings are also disposed to correspond to the exhaust holes. Further, the sealing ring is fixed on the back side of the flow cell through the sealing ring fixing structure. Further, the fixing structure is bonded on the back side of the flow cell through glue such as double-sided adhesive, so as to achieve reliable and effective sealing within an accuracy range of the sealing rings and inlets and outlets. Further, the sealing ring fixing structure includes fixing structures. The sealing ring is fixed on the back side of the flow cell through the sealing ring fixing structure. Further, each fixing structure is a fixing hole, and the sealing ring is disposed in the fixing hole. Further, each sealing ring includes the ring body and the through hole defined in the ring body. The through holes are disposed to correspond to the liquid inlet, the liquid outlet, or the exhaust holes. At least one clamping structure is disposed on the ring body. At least one matching structure is disposed in the fixing hole. The sealing ring is fixed in the fixing hole through matching of the clamping structure and the matching structure. Further, the clamping structure is a bump disposed on the outside of the ring body, and the matching structure is a recessed portion defined in the fixing hole. Or, the clamping structure is a recessed portion defined in the outside of the ring body, and the matching structure is a bump disposed in the fixing hole. Or, the clamping structure is the outer surface of the ring body, and the matching structure is the inner surface of the fixing hole. Further, the sealing ring fixing structure further includes the positioning bump disposed on the fixing structure and sleeved on the outside of the sealing ring. The positioning bump not only assists assembly and placement of the flow cell and the carrying platform, but also reinforces the fixing of the sealing ring to avoid affecting fluid flow when the sealing ring is stressed and deformed. Further, the one-way sealing structure, the normally-closed valve, and/or the valve structure are arranged in the through hole of the sealing ring, which avoids reagent overflow and crystallization on evaporation during the transfer process of the fluid in the flow cell.

In sum, the flow cell provided by the embodiments of the present disclosure has the following beneficial effects: (1) The flow cell makes full use of circular wafers to realize the rapid and effective spreading of reagents under the condition of similar length and width. (2) The flow cell provides a transfer structure between different platforms to ensure high-precision repeated automatic positioning of different platforms. The decoupled optical mechanical platform and the biochemical reaction platform realize sequential or combined operation of multiple sequencing flow cells. (3) The flow cell RFID module is unified with an optically-identifiable label. (4) The sealing ring and the flow cell are assembled integrally without matching clearance.

Even though information and advantages of the present embodiments have been set forth in the foregoing description, together with details of the structures and functions of the present embodiments, the disclosure is illustrative only. Changes may be made in detail, especially in matters of shape, size, and arrangement of parts within the principles of the present exemplary embodiments, to the full extent indicated by the plain meaning of the terms in which the appended claims are expressed.

What is claimed is:

1. A flow cell, comprising:
a flow cell body, wherein the flow cell body comprises a frame and a fluid chamber defined in the flow cell body, the fluid chamber comprises a reaction region allowing a fluid to flow through, a liquid inlet, a liquid outlet, and a plurality of exhaust holes respectively connected to the fluid chamber are defined in the frame, the fluid inputted from the liquid inlet flows through the reaction region in the fluid chamber and flows out through the liquid outlet, the plurality of exhaust holes is configured to discharge gas in the fluid chamber when the fluid flows through the reaction region, the flow cell body comprises an inlet end and an outlet end, the plurality of exhaust holes comprises an inlet-side exhaust hole and an outlet-side exhaust hole, the liquid inlet and the inlet-side exhaust hole are spaced apart from each other on the inlet end, the liquid outlet and the outlet-side exhaust hole are spaced apart from each other on the outlet end, the frame defines an inlet diversion channel, the liquid inlet is connected to the inlet-side exhaust hole through the inlet diversion channel, the inlet diversion channel comprises a bottom surface and an opening opposite to the bottom surface, the opening of the inlet diversion channel is configured to connect the inlet diversion channel to the fluid chamber, the inlet diversion channel comprises two sidewalls connecting the bottom surface and the opening, the two sidewalls comprise a first sidewall close to a middle area of the fluid chamber and a second sidewall far away from the middle area of the fluid chamber, a connecting portion of a top of the first sidewall connected to a surface of a substrate of the frame has a rounded corner, the first sidewall is an inclined plane inclined towards the middle area.

2. The flow cell of claim 1, wherein the inlet-side exhaust hole and the outlet-side exhaust hole are respectively disposed on two sides of a connecting line connecting the liquid inlet and the liquid outlet.

3. The flow cell of claim 1, wherein the fluid chamber is rectangular or square, the liquid inlet and the liquid outlet are disposed on a diagonal of the fluid chamber, the inlet-side exhaust hole and the outlet-side exhaust hole are respectively disposed on two sides of the diagonal, or the inlet-side exhaust hole and the outlet-side exhaust hole are disposed on another diagonal of the fluid chamber.

4. The flow cell of claim 1, wherein
the frame further defines an outlet diversion channel, the liquid outlet is connected to the outlet-side exhaust hole through the outlet diversion channel, the outlet diversion channel comprises a bottom surface and an opening opposite to the bottom surface, the opening of the outlet diversion channel is configured to connect the outlet diversion channel to the fluid chamber.

5. The flow cell of claim 4, wherein the first sidewall close to the opening of the inlet diversion channel has a rounded corner.

6. The flow cell of claim 1, wherein a plurality of supporting points is disposed in the flow cell, the plurality of supporting points is disposed at intervals, the plurality of supporting points is configured to support the fluid chamber to strengthen the flow cell.

7. The flow cell of claim 1, further comprising an outside frame, wherein the outside frame is disposed on an outside of the flow cell, and is configured to allow a mobile device to move the flow cell.

8. The flow cell of claim 7, wherein the outside frame comprises a plurality of grabbing structures, the plurality of grabbing structures is configured to allow the mobile device to move the flow cell; and/or the plurality of grabbing structures is a hole defined in the outside frame; and/or the outside frame comprises a plurality of positioning structures, the plurality of positioning structures is configured to position the flow cell when the mobile device moves and places the flow cell on a carrying platform; and/or the plurality of positioning structures is a plurality of holes defined in the outside frame.

9. The flow cell of claim 7, wherein the outer frame comprises a fixing portion fixed on the flow cell body and a positioning portion disposed outside of the fixing portion, the positioning portion is configured to allow the mobile device to move the flow cell; and/or the positioning portion is configured to position the flow cell when the mobile device moves the flow cell; and/or the positioning portion is configured to position the flow cell when the mobile device moves and places the flow cell on a carrying platform; and/or the positioning portion is sleeved outside of the flow cell body to protect the flow cell body.

10. The flow cell of claim 1, further comprising a plurality of sealing rings, wherein the plurality of sealing rings corresponds to the liquid inlet, the liquid outlet, and the plurality of exhaust holes.

11. The flow cell of claim 10, wherein each of the plurality of sealing rings is fixed on the flow cell through a fixing structure, or each of the plurality of sealing rings is fixed on the flow cell through a fixing hole.

12. The flow cell of claim 11, further comprising a front side and a back side opposite to the front side, wherein the liquid inlet, the liquid outlet, and the plurality of exhaust holes are defined on the back side, wherein the fixing structure or the fixing hole is disposed on a sealing ring fixing structure, the sealing ring fixing structure is fixed or pasted on the back side of the flow cell.

13. The flow cell of claim 12, further comprising a plurality of positioning bumps, wherein each of the plurality of positioning bumps is sleeved on an outside of a corresponding sealing ring and connected to a corresponding fixing structure or fixing hole.

* * * * *